United States Patent
Stransky et al.

(10) Patent No.: US 10,246,750 B2
(45) Date of Patent: Apr. 2, 2019

(54) METHOD FOR DETECTION OF A TECR:PKN1 OR AN ANXA4:PKN1 GENE FUSION

(71) Applicant: BLUEPRINT MEDICINES CORPORATION, Cambridge, MA (US)

(72) Inventors: Nicolas Stransky, Charlestown, MA (US); Joseph L. Kim, Wayland, MA (US)

(73) Assignee: Blueprint Medicines Corporation, Cambridge, MA (US)

(*) Notice: Subject to any disclaimer, the term of this patent is extended or adjusted under 35 U.S.C. 154(b) by 0 days.

(21) Appl. No.: 15/317,679

(22) PCT Filed: Jun. 10, 2015

(86) PCT No.: PCT/US2015/035020
§ 371 (c)(1),
(2) Date: Dec. 9, 2016

(87) PCT Pub. No.: WO2015/191667
PCT Pub. Date: Dec. 17, 2015

(65) Prior Publication Data
US 2017/0114417 A1 Apr. 27, 2017

Related U.S. Application Data

(60) Provisional application No. 62/010,256, filed on Jun. 10, 2014.

(51) Int. Cl.
| | |
|---|---|
| *C12Q 1/6886* | (2018.01) |
| *C07K 14/47* | (2006.01) |
| *C12N 15/11* | (2006.01) |
| *C12Q 1/48* | (2006.01) |
| *C12N 9/12* | (2006.01) |
| *G01N 33/574* | (2006.01) |
| *C12N 9/02* | (2006.01) |
| *C07K 16/40* | (2006.01) |

(52) U.S. Cl.
CPC ........ *C12Q 1/6886* (2013.01); *C07K 14/4721* (2013.01); *C07K 16/40* (2013.01); *C12N 9/001* (2013.01); *C12N 9/12* (2013.01); *C12N 15/11* (2013.01); *C12Q 1/485* (2013.01); *C12Y 103/01093* (2015.07); *C12Y 207/11013* (2013.01); *G01N 33/57423* (2013.01); *G01N 33/57438* (2013.01); *G01N 33/57496* (2013.01); *C07K 2319/00* (2013.01); *C12Q 2600/156* (2013.01); *C12Q 2600/158* (2013.01); *G01N 2333/47* (2013.01); *G01N 2333/90206* (2013.01); *G01N 2333/912* (2013.01); *G01N 2333/9121* (2013.01); *G01N 2500/04* (2013.01); *G01N 2500/10* (2013.01); *G01N 2800/52* (2013.01)

(58) Field of Classification Search
None
See application file for complete search history.

(56) References Cited

U.S. PATENT DOCUMENTS

| | | | | |
|---|---|---|---|---|
| 5,770,421 | A * | 6/1998 | Morris | C07K 14/47 435/194 |
| 9,090,899 | B2 * | 7/2015 | Rubin | C07K 14/47 |
| 2001/0021505 | A1 * | 9/2001 | Morris | C07K 14/47 435/6.11 |
| 2010/0279890 | A1 * | 11/2010 | Lothe | C12Q 1/6837 506/9 |

FOREIGN PATENT DOCUMENTS

| | | |
|---|---|---|
| WO | WO 2004/091479 A2 | 10/2004 |
| WO | WO 2010/081001 A2 | 7/2010 |

OTHER PUBLICATIONS

International Patent Application No. PCT/US2015/035020, filed Jun. 10, 2015, by Blueprint Medicines Corp.: International Search Report and Written Opinion, dated Sep. 10, 2015 (17 pages).
GENBANK Database Accession No. NM_001153, "Homo sapiens annexin A4 (ANXA4), transcript variant 2, MRNA", National Center for Biotechnology Information (NCBI), U.S. National Library of Medicine; PRI Oct. 9, 2016 (6 pages).
GENBANK Database Accession No. NM_002741, "Homo sapiens protein kinase N1 (PKN1), transcript variant 2, mRNA", National Center for Biotechnology Information (NCBI), U.S. National Library of Medicine; PRI Sep. 9, 2016 (9 pages).
GENBANK Database Accession No. NM_138501, "Homo sapiens trans-2,3-enoyl-CoA reductase (TECR), transcript variant 1, mRNA", National Center for Biotechnology Information (NCBI), U.S. National Library of Medicine; PRI Mar. 18, 2016 (5 pages).
Soda, Manabu, et al., "Identification of the transforming EML4-ALK fusion gene in non-small-cell lung cancer," Nature, 448:561-567 (2007).
Köhler, Jens, et al., "Lestaurtinib Inhibits Histone Phosphorylation and Androgen-Dependent Gene Expression in Prostate Cancer Cells", PLOS One, 7(4):e34973 (8 pages) (2012).
Shiga, Kazuhiro, et al., "Development of an intracellularly acting inhibitory peptide selective for PKN", Biochem. J., 425:445-453 (2010).
Metzger, Eric, et al., "Phosphorylation of histone H3 at threonine 11 establishes a novel chromatin mark for transcriptional regulation", Nature Cell Biology, 10(1):53-60 (2008).

(Continued)

*Primary Examiner* — Elly-Gerald Stoica
(74) *Attorney, Agent, or Firm* — Finnegan, Henderson, Farabow, Garrett & Dunner LLP

(57) ABSTRACT

The invention provides to PKN1 gene fusions, PKN1 fusion proteins, and fragments of those genes and polypeptides. The invention further provides methods of diagnosing and treating diseases or disorders associated with PKN1 fusions, such as conditions mediated by aberrant PKN1 expression or activity, or over expression of PKN1.

5 Claims, 4 Drawing Sheets
Specification includes a Sequence Listing.

(56) References Cited

OTHER PUBLICATIONS

Supper, Jochen, et al., "Detecting and visualizing gene fusions", *Methods*, 59:S24-S28 (2013).

Stransky, Nicolas, et al., "The landscape of kinase fusions in cancer", *Nature Communications*, 5:4846, 10 pages (2014).

James, Richard G., et al., "Protein Kinase PKN1 Represses Wnt/β-Catenin Signaling in Human Melanoma Cells", *Journal of Biological Chemistry*, 288(48): 34658-34670 (2013).

* cited by examiner

FIG. 1

```
ATGAAGCATT ACGAG/GTCAC CTTCCGCAAC CCTGTCATTG AGAGGATTCC TCGGCTCCGA   60
CGGCAGAAGA AAATTTTCTC CAAGCAGCAA GGGAAGGCGT TCCAGCGTGC TAGGCAGATG  120
AACATCGATG TCGCCACGTG GGTGCGGCTG CTCCGGAGGC TCATCCCCAA TGCCACGGGC  180
ACAGGCACCT TTAGCCCTGG GGCTTCTCCA GGATCCGAGG CCCGGACCAC GGGTGACATA  240
TCGGTGGAGA AGCTGAACCT CGGCACTGAC TCGGACAGCT CACCTCAGAA GAGCTCGCGG  300
GATCCTCCTT CCAGCCCATC GAGCCTGAGC TCCCCATCC AGGAATCCAC TGCTCCCGAG   360
CTGCCTTCGG AGACCCAGGA GACCCCAGGC CCCGCCCTGT GCAGCCCTCT GAGGAAGTCA  420
CCTCTGACCC TCGAAGATTT CAAGTTCCTG GCGGTGCTGG GCCGGGGTCA TTTTGGGAAG  480
GTGCTCCTCT CCGAATTCCG GCCCAGTGGG GAGCTGTTCG CCATCAAGGC TCTGAAGAAA  540
GGGGACATTG TGGCCCGAGA CGAGGTGGAG AGCCTGATGT GTGAGAAGCG GATATTGGCG  600
GCAGTGACCA GTGCGGGACA CCCCTTCCTG GTGAACCTCT TCGGCTGTTT CCAGACACCG  660
GAGCACGTGT GCTTCGTGAT GGAGTACTCG GCCGGTGGGG ACCTGATGCT GCACATCCAC  720
AGCGACGTGT TCTCTGAGCC CCGTGCCATC TTTTATTCCG CCTGCGTGGT GCTGGGCCTA  780
CAGTTTCTTC ACGAACACAA GATCGTCTAC AGGGACCTGA AGTTGGACAA TTTGCTCCTG  840
GACACCGAGG GCTACGTCAA GATCGCAGAC TTTGGCCTCT GCAAGGAGGG GATGGGCTAT  900
GGGGACCGGA CCAGCACATT CTGTGGGACC CCGGAGTTCC TGGCCCCTGA GGTGCTGACG  960
GACACGTCGT ACACGCGAGC TGTGGACTGG TGGGACTGG GTGTGCTGCT CTACGAGATG   1020
CTGGTTGGCG AGTCCCCATT CCCAGGGGAT GATGAGGAGG AGGTCTTCGA CAGCATCGTC  1080
AACGACGAGG TTCGCTACCC CCGCTTCCTG TCGGCCGAAG CCATCGGCAT CATGAGAAGG  1140
CTGCTTCGGA GGAACCCAGA GCGGAGGCTG GGATCTAGCG AGAGAGATGC AGAAGATGTG  1200
AAGAAACAGC CCTTCTTCAG GACTCTGGGC TGGGAAGCCC TGTTGGCCCG GCGCCTGCCA  1260
CCGCCCTTTG TGCCCACGCT GTCCGGCCGC ACCGACGTCA GCAACTTCGA CGAGGAGTTC  1320
ACCGGGGAGG CCCCCACACT GAGCCCGCCC CGCGACGCGC GGCCCCTCAC AGCCGCGGAG  1380
CAGGCAGCCT TCCTGGACTT CGACTTCGTG GCCGGGGGCT GCTAG
```

(SEQ ID NO:1)

FIG. 2

```
MKHYE/VTFRN PVIERIPRLR RQKKIFSKQQ GKAFQRARQM NIDVATWVRL LRRLIPNATG 60
TGTFSPGASP GSEARTTGDI SVEKLNLGTD SDSSPQKSSR DPPSSPSSLS SPIQESTAPE 120
LPSETQETPG PALCSPLRKS PLTLEDFKFL AVLGRGHFGK VLLSEFRPSG ELFAIKALKK 180
GDIVARDEVE SLMCEKRILA AVTSAGHPFL VNLFGCFQTP EHVCFVMEYS AGGDLMLHIH 240
SDVFSEPRAI FYSACVVLGL QFLHEHKIVY RDLKLDNLLL DTEGYVKIAD FGLCKEGMGY 300
GDRTSTFCGT PEFLAPEVLT DTSYTRAVDW WGLGVLLYEM LVGESPFPGD DEEEVFDSIV 360
NDEVRYPRFL SAEAIGIMRR LLRRNPERRL GSSERDAEDV KKQPFFRTLG WEALLARRLP 420
PPFVPTLSGR TDVSNFDEEF TGEAPTLSPP RDARPLTAAE QAAFLDFDFV AGGC
```

(SEQ ID NO:2)

FIG. 3

ATGGCCATG/A GCTCCCCCAT CCAGGAATCC ACTGCTCCCG AGCTGCCTTC GGAGACCCAG 60
GAGACCCCAG GCCCCGCCCT GTGCAGCCCT CTGAGGAAGT CACCTCTGAC CCTCGAAGAT 120
TTCAAGTTCC TGGCGGTGCT GGGCCGGGGT CATTTTGGGA AGGTGCTCCT CTCCGAATTC 180
CGGCCCAGTG GGGAGCTGTT CGCCATCAAG GCTCTGAAGA AAGGGGACAT TGTGGCCCGA 240
GACGAGGTGG AGAGCCTGAT GTGTGAGAAG CGGATATTGG CGGCAGTGAC CAGTGCGGGA 300
CACCCCTTCC TGGTGAACCT CTTCGGCTGT TTCCAGACAC CGGAGCACGT GTGCTTCGTG 360
ATGGAGTACT CGGCCGGTGG GGACCTGATG CTGCACATCC ACAGCGACGT GTTCTCTGAG 420
CCCCGTGCCA TCTTTTATTC CGCCTGCGTG GTGCTGGGCC TACAGTTTCT TCACGAACAC 480
AAGATCGTCT ACAGGGACCT GAAGTTGGAC AATTTGCTCC TGGACACCGA GGGCTACGTC 540
AAGATCGCAG ACTTTGGCCT CTGCAAGGAG GGGATGGGCT ATGGGGACCG GACCAGCACA 600
TTCTGTGGGA CCCCGGAGTT CCTGGCCCCT GAGGTGCTGA CGGACACGTC GTACACGCGA 660
GCTGTGGACT GGTGGGGACT GGGTGTGCTG CTCTACGAGA TGCTGGTTGG CGAGTCCCCA 720
TTCCCAGGGG ATGATGAGGA GGAGGTCTTC GACAGCATCG TCAACGACGA GGTTCGCTAC 780
CCCCGCTTCC TGTCGGCCGA AGCCATCGGC ATCATGAGAA GGCTGCTTCG GAGGAACCCA 840
GAGCGGAGGC TGGGATCTAG CGAGAGAGAT GCAGAAGATG TGAAGAAACA GCCCTTCTTC 900
AGGACTCTGG GCTGGGAAGC CCTGTTGGCC CGGCGCCTGC CACCGCCCTT TGTGCCCACG 1020
CTGTCCGGCC GCACCGACGT CAGCAACTTC GACGAGGAGT TCACCGGGGA GGCCCCACA 1080
CTGAGCCCGC CCCGCGACGC GCGGCCCCTC ACAGCCGCGG AGCAGGCAGC CTTCCTGGAC 1140
TTCGACTTCG TGGCCGGGGG CTGCTAG (SEQ ID NO:3)

FIG. 4

MAM/SSPIQES TAPELPSETQ ETPGPALCSP LRKSPLTLED FKFLAVLGRG HFGKVLLSEF 60
RPSGELFAIK ALKKGDIVAR DEVESLMCEK RILAAVTSAG HPFLVNLFGC FQTPEHVCFV 120
MEYSAGGDLM LHIHSDVFSE PRAIFYSACV VLGLQFLHEH KIVYRDLKLD NLLLDTEGYV 180
KIADFGLCKE GMGYGDRTST FCGTPEFLAP EVLTDTSYTR AVDWWGLGVL LYEMLVGESP 240
FPGDDEEEVF DSIVNDEVRY PRFLSAEAIG IMRRLLRRNP ERRLGSSERD AEDVKKQPFF 300
RTLGWEALLA RRLPPPFVPT LSGRTDVSNF DEEFTGEAPT LSPPRDARPL TAAEQAAFLD 360
FDFVAGGC (SEQ ID NO:4)

METHOD FOR DETECTION OF A TECR:PKN1 OR AN ANXA4:PKN1 GENE FUSION

CLAIM OF PRIORITY

This application is a national stage application of and claims priority under 35 USC § 371 to International Application No. PCT/US2015/035020, filed Jun. 10, 2015, which claims the benefit of U.S. Provisional Application No. 62/010,256, filed Jun. 10, 2014, the contents of both of which are incorporated herein by reference in their entirety to provide continuity of disclosure.

The instant application contains a Sequence Listing which has been submitted electronically in ASCII format and is hereby incorporated by reference in its entirety. Said ASCII copy, created on Jul. 21, 2015, is named 12386.0007-00304_SL.txt and is 11,484 bytes in size.

This invention relates to PKN1 (Protein Kinase N1) gene fusions and PKN1 fusion proteins. The invention further relates to methods of diagnosing and treating diseases or disorders associated with PKN1 fusions, such as conditions mediated by aberrant PKN1 expression or activity, or conditions associated with overexpression of PKN1.

Many forms of cancer are caused by genetic lesions that give rise to tumor initiation and growth. Genetic lesions may include chromosomal aberrations, such as translocations, inversions, deletions, copy number changes, gene expression level changes, and somatic and germline mutations. Indeed, the presence of such genomic aberrations is a hallmark feature of many cancers, including, for example, B cell cancer, lung cancer, breast cancer, ovarian cancer, pancreatic cancer, and colon cancer. In some models, cancer represents the phenotypic end-point of multiple genetic lesions that endow cells with a full range of biological properties required for tumorigenesis.

Recent efforts by The Cancer Genome Atlas (TCGA), the International Cancer Genome Consortium (ICGC), and dozens of other large-scale profiling efforts have generated an enormous amount of new sequencing data for dozens of cancer types—this includes whole-genome DNA, whole-exome DNA, and full-transcriptome RNA sequencing. These efforts have led to the identification of new driver genes and fusion genes within multiple cancer types. Fusions, particularly fusions involving kinases, are of particular interest, as such fusions have been shown to be oncogenic, and have been successfully targeted by new therapeutics. For example, anaplastic lymphoma kinase (ALK), one of the receptor tyrosine kinases, is known to become oncogenic when fused with various genes. See, e.g., M. Soda et al, "Identification of the transforming EML4-ALK fusion gene in non-small-cell lung cancer," *Nature* 444:561-566 (2007).

A need exists for identifying novel genetic lesions associated with cancer. For example, the presence of fusions involving a kinase in samples collected from more than one source can indicate that the kinase is an oncogenic driver. The identification of such fusions can be an effective approach to diagnosis of cancers and development of compounds, compositions, methods, and assays for evaluating and treating cancer patients.

In one aspect, the invention provides methods for detecting the presence of a PKN1 fusion in a biological sample; the methods include the steps of: (a) obtaining a biological sample from a mammal; and (b) contacting the sample with a reagent that detects a PKN1 fusion, to determine whether a PKN1 fusion is present in the biological sample. In some embodiments, the sample can be from, e.g., a cancer patient. In some embodiments, the cancer is lung cancer, such as, e.g., lung squamous cell carcinoma. In some embodiments, the cancer is liver cancer, such as, e.g., hepatocellular carcinoma. In some embodiments, the fusion can be, e.g., a TECR:PKN1 fusion or an ANXA4:PKN1 fusion. In some embodiments, the TECR:PKN1 fusion has all or a part of the nucleotide and/or amino acid sequence (such as, e.g., the fusion junction) set forth in SEQ ID NO: 1 and SEQ ID NO:2, respectively. In some embodiments, the ANXA4:PKN1 fusion has all or part of the nucleotide and/or amino acid sequence (such as, e.g., the fusion junction) set forth in SEQ ID NO:3 and SEQ ID NO:4, respectively.

In another aspect, the invention provides methods of diagnosing a patient having a disease or disorder associated with aberrant PKN1 expression or activity, or overexpression of PKN1; the methods include: (a) obtaining a biological sample from the patient; and (b) contacting the sample with a reagent that detects a PKN1 fusion to determine whether a PKN1 fusion is present in the biological sample, wherein the detection of the PKN1 fusion indicates the presence of a disorder associated with aberrant PKN1 expression or activity, or overexpression of PKN1.

The invention also includes methods of determining a therapeutic regimen for treating a cancer in a human subject; methods of identifying a patient likely to respond to treatment with a PKN1 inhibitor or a PKN1 fusion inhibitor; methods of stratifying a patient population by detecting a PKN1 fusion; methods of treating a patient; methods of inhibiting the proliferation of cells containing a PKN1 fusion; methods of reducing an activity of a PKN1 fusion; methods of treating a condition mediated by aberrant PKN1 expression or activity; methods of treating a condition characterized by overexpression of PKN1; methods of identifying an agent that modulates the activity of a PKN1 fusion; and methods of monitoring disease burden in a patient having a condition mediated by PKN1.

BRIEF DESCRIPTION OF THE FIGURES

FIG. 1 depicts the nucleotide sequence of a TECR:PKN1 gene fusion (SEQ ID NO: 1) comprising a portion of the TECR gene (NM_138501) up to and including exon 1 (amino acid 5) and a portion of the PKN1 gene (NM_002741) starting at exon 10 (amino acid 474). The underlined codons at nucleotides 13-15 and 16-18 encode the last amino acid of TECR and the first amino acid of PKN1, respectively. The slash between nucleotides 15 and 16 indicates the breakpoint (fusion junction) where translocation and in-frame fusion has occurred.

FIG. 2 depicts the amino acid sequence of a TECR:PKN1 fusion protein (SEQ ID NO:2). The slash between amino acids 5 and 6 indicates the breakpoint or fusion junction between the TECR and PKN1 proteins. Amino acids 5-6 correspond to nucleotides 13-15 and 16-18 in SEQ ID NO:1.

FIG. 3 depicts the nucleotide sequence of an ANXA4:PKN1 gene fusion (SEQ ID NO:3) comprising an ANXA4 gene (NM_001153) up to and including exon 2 (amino acid 3) and a portion of the PKN1 gene (NM_002741) starting at exon 13 (amino acid 578). The underlined codons at nucleotides 7-9 and 10-12 encode the last amino acid of ANXA4 and the first amino acid of PKN1, respectively. The slash between nucleotides 9 and 10 indicates the breakpoint or fusion junction where translocation and in-frame fusion has occurred.

FIG. 4 depicts the amino acid sequence of an ANXA4:PKN1 fusion protein (SEQ ID NO:4). The slash between amino acids 3 and 4 represents the location where the two proteins are fused and corresponds to nucleotides 7-9 and 10-12 of SEQ ID NO:3.

EXEMPLARY EMBODIMENTS OF THE INVENTION

The invention is based, at least in part, on the discovery of novel recombination or translocation events in cancer patients that result in at least a fragment of a PKN1 gene linked to a non-homologous promoter via a recombination or translocation event that may result in aberrant expression (e.g., in a location where the kinase is not typically expressed) or overexpression of the kinase domain of the PKN1 gene and thus, an increase in kinase activity. Thus, a new patient population is identified, which is characterized by the presence of a PKN1 fusion, e.g., a PKN1 gene fusion or fusion protein. This new patient population suffers from or is susceptible to disorders mediated by aberrant PKN1 expression or activity, or overexpression of PKN1, such as, e.g., a cancer. In another aspect of the invention, a new subtype of cancer is identified, which is characterized by the presence of the PKN1 fusions described herein. In some embodiments, the new patient population suffers from or is susceptible to lung cancer (such as, e.g., lung squamous cell carcinoma) or liver cancer (such as, e.g., hepatocellular carcinoma) characterized by the presence of a PKN1 fusion. New methods of diagnosing and treating the patient population and the PKN1 fusion cancer subtype are also provided.

The term "PKN1 fusion" is used generically herein, and includes any fusion molecule (e.g., gene, gene product (e.g., cDNA, mRNA, or protein), and variants thereof) that includes a fragment of PKN1, particularly the coding region for the kinase domain of PKN1, and the coding region of a second, non-homologous gene and a promoter sequence from the non-homologous gene, such that the coding sequence for the kinase domain of PKN1 is under control of the promoter of the non-homologous gene. A PKN1 fusion protein generally includes the kinase domain of PKN1.

PKN1 Gene Fusions and Fusion Proteins

PKN1 encodes a serine/threonine-protein kinase, which is a member of the protein kinase C superfamily. It is believed to be involved in the Rho-dependent signaling pathway and mediates insulin signals to the actin cytoskeleton. Proteolytic activation of this kinase by caspase-3 or related proteases during apoptosis suggests a role in signal transduction related to apoptosis.

PKN1 gene fusions are generated by a fusion between at least a part of the PKN1 gene and a part of another gene as a result of a translocation (including inversion) within a chromosome or between chromosomes. As a result of a translocation, the PKN1 gene may be placed under the transcriptional control of the partner gene promoter, resulting in aberrant PKN1 expression or activity or overexpression of PKN1. The overexpression can lead to certain cancers. Alternatively or additionally, the partner gene may include a dimerization domain that causes PKN1 to become constitutively activated or the fusion event may delete an autoregulatory region of PKN1 leading to a constitutively activated kinase. As used herein, the 5'-region is upstream of, and the 3'-region is downstream of, a fusion junction or breakpoint in one of the component genes. PKN1 and the gene or protein that it is fused to is referred to as "fusion partners." Alternatively, they may be identified as a "PKN1 gene fusion" or a "PKN1 fusion protein" which are collectively termed "PKN1 fusions." The PKN1 fusions disclosed herein have a kinase activity. The phrase "having a kinase activity" as used in this application means having an activity as an enzyme phosphorylating the side chain of an amino acid, such as serine or threonine. In some embodiments, the PKN1 fusion may include PKN1 non-coding sequences (5'UTR), which, when fused in-frame to the fusion partner, results in transcription of nucleotides that are not normally transcribed an introduce amino acids into the fusion protein that are not part of PKN1 or the fusion partner.

In some exemplary embodiments, the fusion partner is all or a portion of TECR (Trans-2,3-Enoyl-CoA Reductase). In other exemplary embodiments, the fusion partner is all or a portion of ANXA4 (Annexin A4).

Reference to "all or a portion" or "all or part" of a PKN1 gene fusion or SEQ ID NO:1 or 3, means that the nucleotide sequence comprises the entire PKN1 gene fusion nucleotide sequence or a fragment of that sequence that comprises the fusion junction or breakpoint between PKN1 and its fusion partner (such as, e.g., TECR or AXNA4). The fragment may comprise 7, 8, 9, 10, 12, 14, 16, 18, 20, 21, 22, 23, 24, 25, 26, 27, 28, 29, 30, 35, 40, 45, 50, 60, 70, 80, 90, 100, 120, 150, 175, 200, 250, 300, or more nucleotides spanning the fusion junction of the PKN1 gene fusion. Reference to "all or a portion" or "all or part" of a PKN1 fusion protein or SEQ ID NO:2 or 4, means an amino acid sequence that comprises the entire PKN1 fusion protein amino acid sequence or a fragment of that sequence that comprises the fusion junction or breakpoint between PKN1 and its fusion partner (such as, e.g., TECR or ANXA4). The fragment may comprise 8, 10, 12, 14, 15, 16, 18, 20, 21, 22, 23, 24, 25, 26, 27, 28, 29, 30, 35, 40, 45, 50, 75, or more amino acids spanning the fusion junction In certain embodiments of the invention, a fusion includes an in-frame fusion of all or a portion of the TECR gene (e.g., a TECR promotor or a functional fragment thereof, and one or more exons encoding TECR or a fragment thereof) and an exon of the PKN1 gene (e.g., one or more exons encoding a PKN1 kinase domain or a functional fragment thereof). Such a fusion can be referred to as a TECR:PKN1 fusion. In one embodiment, the TECR:PKN1 fusion comprises sufficient PKN1 sequence to drive expression of a fusion protein that has kinase activity, e.g., has elevated activity as compared with wild type PKN1 in the same tissue or cell.

In some embodiments, the invention provides a TECR:PKN1 gene fusion comprising the nucleotide sequence depicted in FIG. 1 (SEQ ID NO:1), or a fragment thereof that includes the fusion junction. SEQ ID NO: 1 comprises TECR (NM_138501) up to and including exon 1 (amino acid number 5) fused to PKN1 (NM_002741), beginning at exon 10 (amino acid number 474). In some embodiments the TECR:PKN1 gene fusion comprises a nucleotide sequence that is at least 85%, at least 90%, at least 95%, at least 97%, at least 98%, or at least 99% identical to all or part of SEQ ID NO: 1. In some embodiments, the TECR:PKN1 gene fusion encodes a protein having the sequence depicted in FIG. 2 (SEQ ID NO:2) or a sequence that is at least 85%, at least 90%, at least 95%, at least 97%, at least 989%, or at least 99% identical to all or part of SEQ ID NO:2.

In other embodiments of the invention, a fusion includes an in-frame fusion of all or a portion of the ANXA4 gene (e.g., an ANXA4 promotor or a functional fragment thereof, and one or more exons encoding an ANXA4 or a fragment thereof) and an exon of the PKN1 gene (e.g., one or more exons encoding a PKN1 kinase domain or a functional fragment thereof). Such a fusion can be referred to as an ANXA4:PKN1 fusion. In one embodiment, the ANXA4:PKN1 fusion comprises sufficient PKN1 sequence to drive expression of a fusion protein that has kinase activity, e.g., has elevated activity as compared with wild type PKN1 in the same tissue or cell.

In some embodiments, the invention provides an ANXA4: PKN1 gene fusion comprising the nucleotide sequence depicted in FIG. 3 (SEQ ID NO:3), or a fragment thereof that includes the fusion junction. SEQ ID NO:3 comprises ANXA4 (NM_00153) up to and including exon 2 (amino acid number 3) fused to PKN1 (NM_002741), beginning at exon 13 (amino acid number 578). In some embodiments the ANXA4:PKN1 gene fusion comprises a nucleotide sequence that is at least 85%, at least 90%, at least 95%, at least 97%, at least 98%, or at least 99% identical to all or part of SEQ ID NO:3. In some embodiments, the ANXA4:PKN1 gene fusion encodes a protein having the sequence depicted in FIG. 4 (SEQ ID NO:4) or a sequence that is at least 85%, at least 90%, at least 95%, at least 97%, at least 98%, or at least 99% identical to all or part of SEQ ID NO:4.

The nucleic acid sequences of PKN1 gene fusions may be used as probes, primers, or bait to identify nucleotides from a biological sample that include, flank, or hybridize to, PKN1 fusions, such as TECR:PKN1 (e.g., all or part of SEQ ID NO: 1) or ANXA4:PKN1 (e.g., all or part of SEQ ID NO:3), at, e.g., the fusion junctions. In certain embodiments, the probe, primer, or bait molecule is an oligonucleotide that allows capture, detection, and/or isolation of a PKN1 gene fusion in a biological sample. In certain embodiments, the probes or primers derived from the nucleic acid sequences of PKN1 gene fusions (e.g., from the fusion junctions) may be used, for example, for polymerase chain reaction (PCR) amplification. The oligonucleotide can comprise a nucleotide sequence substantially complementary to a fragment of the PKN1 gene fusion nucleic acid molecules described herein. The sequence identity between the nucleic acid fragment, e.g., the oligonucleotide and the target PKN1 gene fusion sequence, need not be exact, so long as the sequences are sufficiently complementary to allow the capture, detection, and/or isolation of the target sequence. In one embodiment, the nucleic acid fragment is a probe or primer that includes an oligonucleotide between about 5 and 25, e.g., between 10 and 20, or 10 and 15 nucleotides in length that includes the fusion junction of TECR:PKN1 (e.g., all or part of SEQ ID NO: 1) or ANXA4:PKN1 (e.g., all or part of SEQ ID NO:3). In other embodiments, the nucleic acid fragment is a bait that includes an oligonucleotide between about 100 to 300 nucleotides, 130 and 230 nucleotides, or 150 and 200 nucleotides in length that includes the fusion junction of TECR:PKN1 (e.g., all or part of SEQ ID NO: 1) or ANXA4: PKN1 (e.g., all or part of SEQ ID NO:3).

In certain embodiments, the nucleic acid fragments hybridize to a nucleotide sequence that includes a breakpoint or fusion junction, e.g., a breakpoint or fusion junction as identified by a slash ("/") in FIGS. 1 and 3. For example, the nucleic acid fragment can hybridize to a nucleotide sequence that includes the fusion junction between the TECR transcript and the PKN1 transcript (e.g., nucleotides 13-18 of SEQ ID NO:1) or between the ANXA4 transcript and the PKN1 transcript (e.g., nucleotides 7-12 of SEQ ID NO:3), i.e., a nucleotide sequence that includes a portion of SEQ ID NO: 1 or 3. Examples include a nucleotide sequence within exon 1 of a TECR gene and exons 10 to 22 of a PKN1 gene (e.g., a portion of SEQ ID NO:1 comprising nucleotides 13-18, 11-20, 6-25, 1-30, 1-45) or a nucleotide sequence within exons 1-2 of an ANXA4 gene and 13 to 22 of a PKN1 gene (e.g., a portion of SEQ ID NO:3 comprising nucleotides 7-12, 5-15, 1-20, 1-30, or 1-45).

In other embodiments, the nucleic acid fragment includes a bait that comprises a nucleotide sequence that hybridizes to a PKN1 gene fusion nucleic acid molecule described herein, and thereby allows the detection, capture, and/or isolation of the nucleic acid molecule. In one embodiment, a bait is suitable for solution phase hybridization. In other embodiments, a bait includes a binding entity or detection entity, e.g., an affinity tag or fluorescent label, that allows detection, capture, and/or separation, e.g., by binding to a binding entity, of a hybrid formed by a bait and a nucleic acid hybridized to the bait.

In exemplary embodiments, the nucleic acid fragments hybridize to a nucleotide sequence that includes a fusion junction between the TECR transcript and the PKN1 transcript, e.g., a nucleotide sequence within SEQ ID NO:1 comprising nucleotides 13-18 (such as, e.g., a sequence comprising nucleotides 11-20, 6-25, 1-30, or 1-45 of SEQ ID NO:1).

In other exemplary embodiments, the nucleic acid fragments hybridize to a nucleotide sequence that includes a fusion junction between the ANXA4 transcript and the PKN1 transcript, e.g., a nucleotide sequence within SEQ ID NO:3 comprising nucleotides 7-12 (such as, e.g., a sequence comprising nucleotides 5-15, 1-20, 1-30, or 1-45 of SEQ ID NO:3)

Another aspect of the invention provides PKN1 fusion proteins (such as, e.g., a purified or isolated TECR:PKN1 or ANXA4:PKN1 fusion protein), biologically active or antigenic fragments thereof, and use of those polypeptides for detecting and/or modulating the biological activity (such as tumorigenic activity) of a PKN1 fusion protein. Exemplary embodiments of the PKN1 fusion proteins comprise the amino acid sequence set forth in SEQ ID NO:2 or 4, and fragments of those sequences.

In some embodiments, the PKN1 fusion protein of the invention can include a fragment of a TECR protein or an ANXA4 protein. In one embodiment, the PKN1 fusion protein is TECR:PKN1 fusion protein having the amino acid sequence of SEQ ID NO:2 or a fragment thereof, such as, e.g., amino acids 3-8, 1-10, 1-15, 1-20, 1-25, or 1-30 of SEQ ID NO:2. In other embodiments, the PKN1 fusion protein is an ANXA4:PKN1 fusion protein having the amino acid sequence of SEQ ID NO:4 or a fragment thereof, such as, e.g., amino acids 2-6, 1-10, 1-15, 1-20, 1-25, or 1-30 of SEQ ID NO:4.

In some embodiments, the PKN11 fusion protein is a TECR:PKN1 fusion protein comprising an amino acid sequence that is at least 85%, at least 90%, at least 95%, at least 97%, at least 98%, or at least 99% identical to SEQ ID NO:2 or a fragment thereof (e.g., amino acids 3-8, 1-10, 1-15, 1-20, 1-25, or 1-30 of SEQ ID NO:2). In other embodiments, the PKN1 fusion protein is an ANXA4:PKN1 fusion protein comprising an amino acid sequence that is at least 85%, at least 90%, at least 95%, at least 97%, at least 98%, or at least 99% identical to SEQ ID NO:4 or a fragment thereof (e.g., amino acids 2-6, 1-10, 1-15, 1-20, 1-25, or 1-30 of SEQ ID NO:4).

In certain embodiments, the PKN1 fusion protein includes a functional kinase domain. In some embodiments, the PKN1 fusion protein comprises elevated PKN1 activity as compared with wild type PKN1 activity (e.g., in a cancer cell, a non-cancer cell adjacent to the cancer cell, or a non-cancer cell from a control sample, such as a cancer free subject). In one exemplary embodiment, the PKN1 fusion protein is a TECR:PKN1 fusion and includes a PKN1 serine/threonine kinase domain or a functional fragment thereof. In other exemplary embodiments, the PKN1 fusion protein is an ANXA4:PKN1 fusion and includes a PKN1 serine/threonine kinase domain or a functional fragment thereof.

In another embodiment, the PKN1 fusion protein or fragment is a peptide, e.g., an immunogenic peptide or protein, that contains a fusion junction with a heterologous protein as described herein. Such immunogenic peptides or proteins can be used for vaccine preparation for use in the treatment or prevention of cancers caused by or exacerbated by PKN1 gene fusions and PKN1 fusion proteins. In other embodiments, such immunogenic peptides or proteins can be used to raise antibodies specific to the fusion protein. In some embodiments, the PKN1 fusion protein is present in combination with or is further conjugated to one or more adjuvant(s) or immunogen(s), e.g., a protein capable of enhancing an immune response to the PKN1 fusion protein (e.g., a hapten, a toxoid, etc.). In some embodiments, the PKN1 fusion protein is a TECR:PKN1 or ANXA4:PKN1 fusion protein. In some embodiments, the PKN1 fusion protein comprises the fusion junction of SEQ ID NO:2 or 4.

Thus, another aspect of the invention provides an antibody that binds to a PKN1 fusion protein (such as, e.g., a TECR:PKN1 or an ANXA4:PKN1 fusion protein) or a fragment thereof. In certain embodiments, the antibody recognizes a PKN1 fusion protein but does not recognize wild type PKN1 or the wild type fusion partner (such as, e.g., TECR or ANXA4). In some embodiments, the antibody binds to an epitope comprising the junction between PKN1 and the fusion partner (e.g., the junction of TECR:PKN1 or ANXA4:PKN1). In one embodiment, the antibody binds to a TECR:PKN1 fusion protein having the amino acid sequence of SEQ ID NO:2 or a fragment thereof, such as, e.g., amino acids 3-8, 1-10, 1-15, 1-20, 1-25, or 1-30 of SEQ ID NO:2. In other embodiments, the antibody binds to an ANXA4:PKN1 fusion protein having the amino acid sequence of SEQ ID NO:4 or a fragment thereof, such as, e.g., amino acids 2-6, 1-10, 1-15, 1-20, 1-25, or 1-30 of SEQ ID NO:4.

In certain embodiments, the antibodies of the invention inhibit and/or neutralize the biological activity of the PKN1 fusion protein, and more specifically, in some embodiments, the kinase activity of the PKN1 fusion protein. In other embodiments, the antibodies may be used to detect a PKN1 fusion protein or to diagnose a patient suffering from a disease or disorder associated with the expression of a PKN1 fusion protein.

Detection and Diagnostic Methods

In another aspect, the invention provides a method of determining the presence of a PKN1 gene fusion or fusion protein, such as, e.g., a TECR:PKN1 or an ANXA4:PKN1 fusion as described herein. The presence of a PKN1 fusion indicates that the mammal providing the biological sample suffers from or is at risk of developing a disorder mediated by aberrant PKN1 expression or activity, or overexpression of PKN1, such as, e.g., a cancer. The presence of a PKN1 fusion may also indicate that the cancer is treatable with a PKN1 inhibitor (such as, e.g., a kinase inhibitor or an antibody specific to PKN1) or a PKN1 fusion inhibitor. In some embodiments, the cancer is lung cancer. In some embodiments, the cancer is liver cancer. In some embodiments, the PKN1 fusion present in the sample is TECR:PKN1 and the cancer to be treated is lung squamous cell carcinoma. In other embodiments, the PKN1 fusion present in the sample is ANXA4:PKN1 and the cancer to be treated is hepatocellular carcinoma.

In one embodiment, the PKN1 fusion detected is a nucleic acid molecule or a polypeptide. The method includes detecting whether a PKN1 fusion nucleic acid molecule or polypeptide is present in a cell (e.g., a circulating cell or a cancer cell), a tissue (e.g., a tumor), or a sample, e.g., a tumor sample, from a subject. In one embodiment, the sample is a nucleic acid sample. In one embodiment, the nucleic acid sample comprises DNA, e.g., genomic DNA or cDNA, or RNA, e.g., mRNA. In other embodiments, the sample is a protein sample.

The sample can be chosen from one or more sample types, such as, for example, tissue, e.g., cancerous tissue (e.g., a tissue biopsy), whole blood, serum, plasma, buccal scrape, sputum, saliva, cerebrospinal fluid, urine, stool, circulating tumor cells, circulating nucleic acids, or bone marrow.

I. Methods for Detecting Gene Fusions

In certain embodiments, the sample is acquired from a subject having or at risk of having a cancer (e.g., a patient), or alternatively, the method further includes acquiring a sample from the subject. In some embodiments, the PKN1 fusion is detected in a nucleic acid molecule by a method chosen from one or more of: nucleic acid hybridization assay (e.g. in situ hybridization, comparative genomic hybridization, microarray, Southern blot, northern blot), amplification-based assays (e.g., PCR, PCR-RFLP assay, or real-time PCR), sequencing and genotyping (e.g. sequence-specific primers, high-performance liquid chromatography, or mass-spectrometric genotyping), and screening analysis (including metaphase cytogenetic analysis by karyotype methods).

(1) Hybridization Methods

In some embodiments, the reagent hybridizes to a PKN1 gene fusion, such as, e.g., nucleotides 13-18, 11-20, 6-25, 1-30, or 1-45 of SEQ ID NO:1. In alternate embodiments, the reagent detects the presence of nucleotides 7-12, 5-15, 1-20, 1-30, or 1-45 of SEQ ID NO:3. In one embodiment, the method includes: contacting a nucleic acid sample, e.g., a genomic DNA sample (e.g., a chromosomal sample or a fractionated, enriched or otherwise pre-treated sample) or a gene product (mRNA, cDNA), obtained from the subject, with a nucleic acid fragment e.g., a probe or primer as described herein (e.g., an exon-specific or a breakpoint-specific probe or primer) under conditions suitable for hybridization, and determining the presence or absence of the PKN1 gene fusion, such as, e.g. TECR:PKN1 or ANXA4:PKN1. In an alternate embodiment, the method includes the steps of obtaining a sample; exposing the sample to a nucleic acid probe which hybridizes to an mRNA or cDNA encoding a PKN1 fusion protein that comprises amino acids 3-8, 1-10, 1-15, 1-20, 1-25, or 1-30 of SEQ ID NO:2, or amino acids 2-6, 1-10, 1-15, 1-20, 1-25, or 1-30 of SEQ ID NO:4.

Hybridization, as described throughout the specification, may be carried out under stringent conditions, e.g., medium or high stringency. See, e.g., J. Sambrook, E. F. Fritsch, and T. Maniatis, *Molecular Cloning: A Laboratory Manual*, Cold Spring Harbor Laboratory Pr; 2nd edition (1989); T. Brown, *Hybridization Analysis of DNA Blots. Current Protocols in Molecular Biology* at 21:2.10.1-2.10.16 (2001). High stringency conditions for hybridization refer to conditions under which two nucleic acids must possess a high degree of base pair homology to each other in order to hybridize. Examples of highly stringent conditions for hybridization include hybridization in 4-sodium chloride/ sodium citrate (SSC), at 65 or 70° C., or hybridization in 4×SSC plus 50% formamide at about 42 or 50° C., followed by at least one, at least two, or at least three washes in 1×SSC, at 65 or 70° C. Another example of highly stringent conditions includes hybridization in 2×SSC; 10×Denhardt solution (Fikoll 400+PEG+BSA; ratio 1:1:1) 0.1% SDS; 5 mM EDTA; 50 mM Na$_2$HPO$_4$; 250 µg/ml of herring sperm DNA; 50 µg/ml of tRNA; or 0.25 M of sodium phosphate buffer, pH 7.2; 1 mM EDTA7% SDS at 60° C.; followed by washing 2×SSC, 0.1% SDS at 60° C.

The nucleic acid fragments can be detectably labeled with, e.g., a radiolabel, a fluorescent label, a bioluminescent label, a chemiluminescent label, an enzyme label, a binding pair label (e.g., biotin/streptavidin), an antigen label, or can include an affinity tag, or identifier (e.g., an adaptor, barcode or other sequence identifier). Labeled or unlabeled nucleic acids and/or nucleic acid fragments may be used in reagents for detecting, capturing, or isolating PKN1 gene fusions. Labeled or unlabeled nucleic acids and/or nucleic acid fragments may be used in reagents for detecting, capturing, and/or isolating PKN1 gene fusions, such as, e.g., TECR:PKN1 (e.g., all or part of SEQ ID NO: 1) or ANXA4:PKN1 (e.g., all or part of SEQ ID NO:3). In some embodiments, the labeled reagent can be detected using, e.g., autoradiography, microscopy (e.g., brightfield, fluorescence, or electron microscopy), enzyme-linked immunosorbent assay (ELISA), or immunohistochemistry.

In some embodiments, the method comprises performing chromosome in situ hybridization with chromosomal DNA from a biological sample to detect the presence of a PKN1 gene fusion (such as, e.g., TECR:PKN1 or ANXA4:PKN1, as disclosed herein). In some embodiments, the chromosome in situ hybridization comprises the steps of: providing a chromosome (e.g., interphase or metaphase chromosome) preparation (e.g., by attaching the chromosomes to a substrate (e.g., glass)); denaturing the chromosomal DNA (e.g., by exposure to formamide) to separate the double strands of the polynucleotides from each other; exposing the nucleic acid probe to the chromosomes under conditions to allow hybridization of the probe to the target DNA; removing unhybridized or non-specifically hybridized probes by washing; and detecting the hybridization of the probe with the target DNA. In some embodiments, the chromosome in situ hybridization is fluorescence in situ hybridization (FISH). In some embodiments, the probe is labeled directly by a fluorescent label, or indirectly by incorporation of a nucleotide containing a tag or reporter molecule (e.g., biotin, digoxigenin, or hapten) which after hybridization to the target DNA is then bound by fluorescently labeled affinity molecule (e.g., an antibody or streptavidin). In some embodiments, the hybridization of the probe with the target DNA in FISH can be visualized using a fluorescence microscope.

In other embodiments, the method comprises performing Southern blot with DNA polynucleotides from a biological sample to detect the presence of a PKN1 gene fusion (such as, e.g., TECR:PKN1 or ANXA4:PKN1, as disclosed herein). In some embodiments, the Southern blot comprises the steps of: optionally fragmenting the polynucleotides into smaller sizes by restriction endonucleases; separating the polynucleotides by gel electrophoresis; denaturing the polynucleotides (e.g., by heat or alkali treatment) to separate the double strands of the polynucleotides from each other; transferring the polynucleotides from the gel to a membrane (e.g., a nylon or nitrocellulose membrane); immobilizing the polynucleotides to the membrane (e.g., by UV light or heat); exposing the nucleic acid probe to the polynucleotides under conditions to allow hybridization of the probe to the target DNA; removing unhybridized or non-specifically hybridized probes by washing; and detecting the hybridization of the probe with the target DNA.

(2) Amplification-Based Assays

In certain embodiments, the method of determining the presence of a PKN1 gene fusion, comprises (a) performing a PCR amplification reaction with polynucleotides from a biological sample, wherein the amplification reaction utilizes a pair of primers which will amplify at least a fragment of the PKN1 gene fusion, wherein the fragment comprises the fusion junction, wherein the first primer is in sense orientation and the second primer is in antisense orientation; and (b) detecting an amplification product, wherein the presence of the amplification product is indicative of the presence of a PKN1 fusion polynucleotide in the sample. In specific exemplary embodiments, the PKN1 gene fusion is TECR:PKN1, such as, e.g., the gene fusion of SEQ ID NO: 1 or a fragment thereof comprising nucleotides 13-18, 11-20, 6-25, 1-30, or 1-45 of SEQ ID NO:1 In other exemplary embodiments, the gene fusion is ANXA4:PKN1 such as, e.g. the gene fusion of SEQ ID NO:3 or a fragment thereof comprising nucleotides 7-12, 5-15, 1-20, 1-30, or 1-45 of SEQ ID NO:3.

In some embodiments, step (a) of performing a PCR amplification reaction comprises: (i) providing a reaction mixture comprising the polynucleotides (e.g., DNA or cDNA) from the biological sample, the pair of primers which will amplify at least a fragment of the PKN1 gene fusion wherein the first primer is complementary to a sequence on the first strand of the polynucleotides and the second primer is complementary to a sequence on the second strand of the polynucleotides, a DNA polymerase, and a plurality of free nucleotides comprising adenine, thymine, cytosine, and guanine (dNTPs); (ii) heating the reaction mixture to a first predetermined temperature for a first predetermined time to separate the double strands of the polynucleotides from each other; (iii) cooling the reaction mixture to a second predetermined temperature for a second predetermined time under conditions to allow the first and second primers to hybridize with their complementary sequences on the first and second strands of the polynucleotides, and to allow the DNA polymerase to extend the primers; and (iv) repeating steps (ii) and (iii) for a predetermined number of cycles (e.g., 10, 15, 20, 25, 30, 35, 40, 45, or 50 cycles).

In some embodiments, the polynucleotides from the biological sample comprise RNA, and the method further comprises performing a RT-PCR amplification reaction with the RNA to synthesize cDNA as the template for subsequent or simultaneous PCR reactions. In some embodiments, the RT-PCR amplification reaction comprises providing a reaction mixture comprising the RNA, a primer which will amplify the RNA (e.g., a sequence-specific primer, a random primer, or oligo(dT)s), a reverse transcriptase, and dNTPs, and heating the reaction mixture to a third predetermined temperature for a third predetermined time under conditions to allow the reverse transcriptase to extend the primer.

(3) Sequencing and Genotyping

Another method for determining the presence of a PKN1 gene fusion molecule (such as, e.g., TECR:PKN1 or ANXA4:PKN1, as disclosed herein) includes: sequencing a portion of the nucleic acid molecule (e.g., sequencing the portion of the nucleic acid molecule that comprises the fusion junction of a PKN1 gene fusion), thereby determining that the PKN1 gene fusion is present in the nucleic acid molecule. Optionally, the sequence acquired is compared to a reference sequence, or a wild type reference sequence. In one embodiment, the sequence is determined by a next generation sequencing method. In some embodiments, the sequencing is automated and/or high-throughput sequencing. The method can further include acquiring, e.g., directly or indirectly acquiring, a sample, e.g., a tumor or cancer sample, from a patient.

In some embodiments, the sequencing comprises chain terminator sequencing (Sanger sequencing), comprising: providing a reaction mixture comprising a nucleic acid molecule from a biological sample, a primer complementary to a region of the template nucleic acid molecule, a DNA polymerase, a plurality of free nucleotides comprising adenine, thymine, cytosine, and guanine (dNTPs), and at least one chain terminating nucleotide (e.g., at least one di-deoxynucleotide (ddNTPs) chosen from ddATP, ddTTP, ddCTP, and ddGTP), wherein the at least one chain terminating nucleotide is present in a low concentration so that chain termination occurs randomly at any one of the positions containing the corresponding base on the DNA strand; annealing the primer to a single strand of the nucleic acid molecule; extending the primer to allow incorporation of the chain terminating nucleotide by the DNA polymerase to produce a series of DNA fragments that are terminated at positions where that particular nucleotide is used; separating the polynucleotides by electrophoresis (e.g., gel or capillary electrophoresis); and determining the nucleotide order of the template nucleic acid molecule based on the positions of chain termination on the DNA fragments. In some embodiments, the sequencing is carried out with four separate base-specific reactions, wherein the primer or the chain terminating nucleotide in each reaction is labeled with a separate fluorescent label. In other embodiments, the sequencing is carried out in a single reaction, wherein the four chain terminating nucleotides mixed in the single reaction are each labeled with a separate fluorescent label.

In some embodiments, the sequencing comprises pyrosequencing (sequencing by synthesis), comprising: (i) providing a reaction mixture comprising a nucleic acid molecule from a biological sample, a primer complementary to a region of the template nucleic acid molecule, a DNA polymerase, a first enzyme capable of converting pyrophosphate into ATP, and a second enzyme capable using ATP to generates a detectable signal (e.g., a chemiluminescent signal, such as light) in an amount that is proportional to the amount of ATP; (ii) annealing the primer to a single strand of the nucleic acid molecule: (iii) adding one of the four free nucleotides (dNTPs) to allow incorporation of the correct, complementary dNTP onto the template by the DNA polymerase and release of pyrophosphate stoichiometrically; (iv) converting the released pyrophosphate to ATP by the first enzyme; (v) generating a detectable signal by the second enzyme using the ATP; (vi) detecting the generated signal and analyzing the amount of signal generated in a pyrogram; (vii) removing the unincorporated nucleotides; and (viii) repeating steps (iii) to (vii). The method allows sequencing of a single strand of DNA, one base pair at a time, and detecting which base was actually added at each step. The solutions of each type of nucleotides are sequentially added and removed from the reaction. Light is produced only when the nucleotide solution complements the first unpaired base of the template. The order of solutions which produce detectable signals allows the determination of the sequence of the template.

In some embodiments, the method of determining the presence of a PKN1 fusion (such as, e.g., TECR:PKN1 or ANXA4:PKN1, as disclosed herein) comprises analyzing a nucleic acid sample (e.g., DNA, cDNA, or RNA, or an amplification product thereof) by HPLC. The method may comprise: passing a pressurized liquid solution containing the sample through a column filled with a sorbent, wherein the nucleic acid or protein components in the sample interact differently with the sorbent, causing different flow rates for the different components; separating the components as they flow out the column at different flow rates. In some embodiments, the HPLC is chosen from, e.g., reverse-phase HPLC, size exclusion HPLC, ion-exchange HPLC, and bioaffinity HPLC.

In some embodiments, the method of determining the presence of a PKN1 fusion (such as, e.g., TECR:PKN1 or ANXA4:PKN1, as disclosed herein) comprises analyzing a nucleic acid sample (e.g., DNA, cDNA, or RNA, or an amplification product thereof) by mass spectrometry. The method may comprise: ionizing the components in the sample (e.g., by chemical or electron ionization); accelerating and subjecting the ionized components to an electric or magnetic field; separating the ionized components based on their mass-to-charge ratios; and detecting the separated components by a detector capable of detecting charged particles (e.g., by an electron multiplier).

II. Methods for Detecting Fusion Proteins

Another aspect of the invention provides a method of determining the presence of a PKN1 fusion protein in a mammal. The method comprises the steps of obtaining a biological sample of a mammal (such as, e.g., a human cancer), and exposing that sample to at least one reagent that detects a PKN1 fusion protein (e.g., an antibody that recognizes the PKN1 fusion but does not recognize the wild type PKN1 or the wild type fusion partner) to determine whether a PKN1 fusion protein is present in the biological sample. The detection of a PKN1 fusion protein indicates the presence of a mutant PKN1 in the mammal (such as, e.g., in the human cancer). In some embodiments, the PKN1 fusion protein comprises an amino acid sequence having at least 85%, 90%, 95%, 97%, 98%, or 99% identity with an amino acid sequence of all or part of SEQ ID NO:2 or 4 or fragments thereof that include the fusion junction. In some embodiments the cancer is lung cancer (such as, e.g., lung squamous cell carcinoma). In some embodiments, the cancer is liver cancer (such as, e.g., hepatocellular carcinoma).

In some embodiments, the reagent that detects a PKN1 fusion protein can be detectably labeled with, e.g., a radiolabel, a fluorescent label, a bioluminescent label, a chemiluminescent label, an enzyme label, a binding pair label (e.g., biotin/streptavidin), an antigen label, or can include an affinity tag or identifier (e.g., an adaptor, barcode or other sequence identifier). In some embodiments, the labeled reagent can be detected using, e.g., autoradiography, microscopy (e.g., brightfield, fluorescence, or electron microscopy), ELISA, or immunohistochemistry. In some embodiments, the PKN1 fusion protein is detected in a biological sample by a method chosen from one or more of: antibody-based detection (e.g., western blot, ELISA, immunohistochemistry), size-based detection methods (e.g., HPLC or mass spectrometry), or protein sequencing.

(1) Antibody-Based Detection

In some embodiments, the method comprises performing a western blot with polypeptides from a biological sample to detect the presence of a PKN1 fusion protein (such as, e.g., TECR:PKN1 or ANXA4:PKN1, as disclosed herein). In some embodiments, the western blot comprises the steps of: separating the polypeptides by gel electrophoresis; transferring the polypeptides from the gel to a membrane (e.g., a nitrocellulose or polyvinylidene difluoride (PVDF) membrane); blocking the membrane to prevent nonspecific binding by incubating the membrane in a dilute solution of protein (e.g., 3-5% bovine serum albumin (BSA) or non-fat dry milk in Tris-Buffered Saline (TBS) or I-Block, with a minute percentage (e.g., 0.1%) of detergent, such as, e.g., Tween 20 or Triton X-100); exposing the polypeptides to at least one reagent that detects a PKN1 fusion protein (e.g., an antibody that recognizes the PKN1 fusion but does not recognize the wild type PKN1 or the wild type fusion partner); removing unbound or non-specifically bound reagent by washing; and detecting the binding of the reagent with the target protein. In some embodiments, the method comprises two-step detection; exposing the polypeptides to a primary antibody that specifically binds to a PKN1 fusion protein; removing unbound or non-specifically bound primary antibody by washing; exposing the polypeptides to a secondary antibody that recognizes the primary antibody; removing unbound or non-specifically bound secondary antibody by washing; and detecting the binding of the secondary antibody. In some embodiments, the reagent that detects a PKN1 fusion protein (e.g., the fusion specific antibody, or the secondary antibody) is directly labeled for detection. In other embodiments, the reagent is linked to an enzyme, and the method further comprises adding a substrate of the enzyme to the membrane; and developing the membrane by detecting a detectable signal produced by the reaction between the enzyme and the substrate. For example, the reagent may be linked with horseradish peroxidase to cleave a chemiluminescent agent as a substrate, producing luminescence in proportion to the amount of the target protein for detection.

In some embodiments, the method comprises performing ELISA with polypeptides from a biological sample to detect the presence of a PKN1 fusion protein (such as, e.g., TECR:PKN1 or ANXA4:PKN1, as disclosed herein). In some embodiments, the ELISA is chosen from, e.g., direct ELISA, indirect ELISA, sandwich ELISA, and competitive ELISA.

In one embodiment, the direct ELISA comprises the steps of: attaching polypeptides from a biological sample to a surface; blocking the surface to prevent nonspecific binding by incubating the surface in a dilute solution of protein; exposing the polypeptides to an antibody that specifically binds to a PKN1 fusion protein (e.g., an antibody that recognizes the PKN1 fusion (such as, e.g., TECR:PKN1 or ANXA4:PKN1, as disclosed herein) but does not recognize the wild type PKN1 or the wild type fusion partner); removing unbound or non-specifically bound antibody by washing; and detecting the binding of the antibody with the target protein. In some embodiments, the antibody is directly labeled for detection. In other embodiments, the antibody is linked to an enzyme, and the method further comprises adding a substrate of the enzyme; and detecting a detectable signal produced by the reaction between the enzyme and the substrate.

In another embodiment, the indirect ELISA comprises the steps of: attaching polypeptides from a biological sample to a surface; blocking the surface to prevent nonspecific binding by incubating the surface in a dilute solution of protein; exposing the polypeptides to a primary antibody that specifically binds to a PKN1 fusion protein (such as, e.g., TECR:PKN1 or ANXA4:PKN1, as disclosed herein); removing unbound or non-specifically bound primary antibody by washing; exposing the polypeptides to a secondary antibody that recognizes the primary antibody; removing unbound or non-specifically bound secondary antibody by washing; and detecting the binding of the secondary antibody. In some embodiments, the secondary antibody is directly labeled for detection. In other embodiments, the secondary antibody is linked to an enzyme, and the method further comprises adding a substrate of the enzyme; and detecting a detectable signal produced by the reaction between the enzyme and the substrate.

In some embodiments, the method comprises performing immunohistochemistry with polypeptides from a biological sample to detect the presence of a PKN1 fusion protein (such as, e.g., TECR:PKN1 or ANXA4:PKN1, as disclosed herein). In some embodiments, the immunohistochemistry comprises the steps of: fixing a cell or a tissue section (e.g., by paraformaldehyde or formalin treatment); permeabilizing the cell or tissue section to allow target accessibility; blocking the cell or tissue section to prevent nonspecific binding; exposing the cell or tissue section to at least one reagent that detects a PKN1 fusion protein (e.g., an antibody that recognizes the PKN1 fusion but does not recognize the wild type PKN1 or the wild type fusion partner); removing unbound or non-specifically bound reagent by washing; and detecting the binding of the reagent with the target protein. In some embodiments, the reagent is directly labeled for detection. In other embodiments, the reagent is linked to an enzyme, and the method further comprises adding a substrate of the enzyme; and detecting a detectable signal produced by the reaction between the enzyme and the substrate. In some embodiments, the immunohistochemistry may comprise the two-step detection as in the indirect ELISA.

(2) Size-Based Detection Methods

In some embodiments, the method of determining the presence of a PKN1 fusion (such as, e.g., TECR:PKN1 or ANXA4:PKN1, as disclosed herein) comprises analyzing a protein sample by HPLC. The method may comprise: passing a pressurized liquid solution containing the sample through a column filled with a sorbent, wherein the nucleic acid or protein components in the sample interact differently with the sorbent, causing different flow rates for the different components; separating the components as they flow out the column at different flow rates. In some embodiments, the HPLC is chosen from, e.g., reverse-phase HPLC, size exclusion HPLC, ion-exchange HPLC, and bioaffinity HPLC.

In some embodiments, the method of determining the presence of a PKN1 fusion (such as, e.g., TECR:PKN1 or ANXA4:PKN1, as disclosed herein) comprises analyzing a protein sample by mass spectrometry. The method may comprise: ionizing the components in the sample (e.g., by chemical or electron ionization); accelerating and subjecting the ionized components to an electric or magnetic field; separating the ionized components based on their mass-to-charge ratios; and detecting the separated components by a detector capable of detecting charged particles (e.g., by an electron multiplier).

Detection of a PKN1 gene fusion or a PKN1 fusion protein in a patient can lead to assignment of the patient to the newly identified patient population that bears the PKN1 fusion. Because this patient population can suffer from or be susceptible to a disorder associated with an aberrant PKN1 expression or activity or overexpression of PKN1, detection of the PKN1 fusion can also lead to diagnosis of such disorder. Thus, a further aspect of the invention provides a method of stratifying a patient population (e.g., assigning a patient, to a group or class) and/or diagnosing a patient, comprising: obtaining a biological sample from the patient, contacting the sample with at least one reagent that detects a PKN1 gene fusion or a PKN1 fusion protein to determine whether a PKN1 fusion is present in the biological sample. The detection of a PKN1 fusion indicates that the patient belongs to the newly identified patient population that bears the PKN1 fusion, and/or the presence of a disorder associated with aberrant PKN1 expression or activity or overexpression of PKN1, such as e.g., a cancer. The detection of a PKN1 fusion also identifies a new subtype of cancer, which is characterized by the presence of the PKN1 fusion. In some embodiments, the cancer is lung cancer (such as, e.g., lung squamous cell carcinoma). In some embodiments, the cancer is liver cancer (such as, e.g., hepatocellular carcinoma). Thus, the method may further comprise diagnosing the disorder as treatable with a PKN1 inhibitor or a PKN1 fusion inhibitor if the PKN1 fusion is detected. In certain embodiments, the PKN1 fusion is TECR:PKN1. In other embodiments, the PKN1 fusion is ANXA4:PKN1. In some embodiments, the TECR:PKN1 fusion has all or a part of the nucleotide and/or amino acid sequence (such as, e.g., the fusion junction) set forth in SEQ ID NO:1 and SEQ ID NO:2, respectively. In some embodiments, the ANXA4:PKN1 fusion has all or part of the nucleotide and/or amino acid sequence (such as, e.g., the fusion junction) set forth in SEQ ID NO:3 and SEQ ID NO:4, respectively.

In some embodiments, the PKN1 gene fusion or PKN1 fusion protein is detected prior to initiating, during, or after, a treatment of a patient with, e.g., a PKN1 inhibitor or a PKN1 fusion inhibitor. In one embodiment, the PKN1 gene fusion or PKN1 fusion protein is detected at the time the patient is diagnosed with a cancer. In other embodiment, the PKN1 fusion is detected at a pre-determined interval, e.g., a first point in time and at least at a subsequent point in time. In certain embodiments, in response to detection of a PKN1 fusion, such as, e.g., TECR:PKN1 or ANXA4:PKN1, the method further includes one or more of:

(1) stratifying a patient population (e.g., assigning a patient, to a group or class);

(2) identifying or selecting the patient as likely or unlikely to respond to a treatment, e.g., a PKN1-specific inhibitor treatment (e.g., a kinase inhibitor treatment), or a PKN1 fusion inhibitor treatment as described herein:

(3) selecting a treatment regimen, e.g., administering or not administering a preselected therapeutic agent, such as, e.g., a PKN1 inhibitor, or a PKN1 fusion inhibitor;

(4) prognosticating the time course of the disease in the patient (e.g., evaluating the likelihood of increased or decreased patient survival); or (5) monitoring the effectiveness of treatment (e.g., by detecting a reduction in the level of PKN1 gene fusion or fusion protein in a patient sample).

In certain embodiments, upon detection of a PKN1 gene fusion or PKN1 fusion protein in a patient's biological sample, the patient is identified as likely to respond to a treatment that comprises a PKN1 inhibitor or a PKN1 fusion inhibitor. In some embodiments, the PKN1 fusion detected is a TECR:PKN1 fusion. In alternate embodiments the PKN1 fusion detected is an ANXA4:PKN1 fusion.

A further aspect of the invention provides a method of selecting a treatment option by detecting a PKN1 fusion. The method comprises obtaining a biological sample from a patient and exposing the sample to at least one reagent that detects a PKN1 gene fusion or fusion protein to determine whether a PKN1 fusion is present in the biological sample. The detection of the PKN1 fusion indicates the likelihood of the patient responding to treatment with a PKN1 inhibitor, or a PKN1 fusion inhibitor. The method may be augmented or personalized by evaluating the effect of a variety of kinase, PKN1 or PKN1 fusion inhibitors on the biological sample shown to contain a PKN1 fusion to determine the most appropriate inhibitor to administer. In certain embodiments, the PKN1 fusion is TECR:PKN1. In other embodiments, the PKN1 fusion is ANXA4:PKN1. In some embodiments, the TECR:PKN1 fusion has all or a part of the nucleotide and/or amino acid sequence (such as, e.g., the fusion junction) set forth in SEQ ID NO:1 and SEQ ID NO:2, respectively. In some embodiments, the ANXA4:PKN1 fusion has all or part of the nucleotide and/or amino acid sequence (such as, e.g., the fusion junction) set forth in SEQ ID NO:3 and SEQ ID NO:4, respectively.

Methods of Treatment

Alternatively, or in combination with the detection and diagnostic methods described herein, the invention provides method for treating the newly identified patient population and the new PKN1 fusion cancer subtype, which are characterized by the presence of a PKN1 fusion. The patient population and cancer subtype can be associated with or predict the onset of a condition mediated by aberrant PKN1 expression or activity, or overexpression of PKN1, such as, e.g., a cancer or a tumor harboring a PKN1 fusion. The methods comprise administering a therapeutic agent, e.g., a PKN1 inhibitor, such as e.g., a kinase inhibitor or an antibody specific to PKN1; or a PKN1 fusion inhibitor, i.e., an inhibitor that blocks the activity of the PKN1 fusion but not wild type PKN1 or wild type fusion partner (e.g., TECR or ANXA4), such as, e.g., an antibody specific to a TECR:PKN1 or an ANXA4:PKN1 fusion protein, e.g., any one of the antibodies described above, or an RNA inhibitor that recognizes PKN1 or the fusion junction of a PKN1 gene fusion, including but not limited to siRNA, dsRNA, shRNA, or any other antisense nucleic acid inhibitor, alone or in combination with e.g., other chemotherapeutic agents or procedures, in an amount sufficient to treat a condition mediated by aberrant PKN1 expression or activity, or overexpression of PKN1 by one or more of the following: impeding growth of a cancer, causing a cancer to shrink by weight or volume, extending the expected survival time of the patient, inhibiting tumor growth, reducing tumor mass, reducing size or number of metastatic lesions, inhibiting the development of new metastatic lesions, prolonging survival, prolonging progression-free survival, prolonging time to progression, and/or enhancing quality of life.

In certain embodiments, the PKN1 fusion of the invention may be inhibited by a PKN1 inhibitor or a PKN1 fusion inhibitor. In some embodiments, the therapeutic agent is a PKN1 inhibitor, such as, e.g., a compound, biological or chemical, which inhibits, directly or indirectly, the expression and/or activity of PKN1. For example, the PKN1 inhibitors may be an antibody (such as, e.g., antibodies specific to PKN1) or a small molecule inhibitor (such as, e.g., a kinase inhibitor). In some embodiments, the inhibitors may act directly on PKN1 itself, modify the activity of PKN1, or inhibit the expression of PKN1. In other embodiments, the inhibitors may indirectly inhibit PKN1 activity by inhibiting the activity of proteins or molecules other than PKN1 itself. For example, the inhibitors may modulate the activity of regulatory kinases that phosphorylate or dephosphorylate PKN1, interfere with binding of ligands, or inhibit the activity of interacting or downstream proteins or molecules.

In some embodiments, the PKN1 fusion is inhibited by a PKN1 fusion inhibitor, such as, e.g., an antibody that recognizes all or part of a PKN1 fusion (such as, e.g., TECR:PKN1 or ANXA4:PKN1, as described herein) but does not recognize wild type PKN1 or wild type fusion partner (e.g., TECR or ANXA4). In some embodiments, the PKN1 fusion protein (such as, e.g., TECR:PKN1 or ANXA4:PKN1, as described herein) is inhibited by an agent that inhibits transcription or translation of the fusion protein, e.g., an RNA inhibitor that recognizes the PKN1 coding sequence, the binding partner (e.g., TECR or ANXA4), or the binding partner; PKN1 fusion junction, including but not limited to small interfering RNA (siRNA), double stranded RNA (dsRNA), short-hairpin RNA (shRNA), or any other antisense nucleic acid inhibitor. In some embodiments, the PKN1 fusion inhibited is selected from all or a portion of any one of SEQ ID NOs: 1-4.

As used herein, and unless otherwise specified, a "therapeutically effective amount" of a compound is an amount sufficient to provide a therapeutic benefit in the treatment or management of a condition mediated by aberrant PKN1 expression or activity, or overexpression of PKN1, such as, delaying or minimizing one or more symptoms associated with a cancer or a tumor harboring a PKN1 fusion (such as, e.g., TECR:PKN1 or ANXA4:PKN1, as described herein). A therapeutically effective amount of a compound means an amount of therapeutic agent, alone or in combination with other therapeutic agents, which provides a therapeutic benefit in the treatment or management of the cancer. The term "therapeutically effective amount" can encompass an amount that improves overall therapy, reduces or avoids symptoms or causes of the condition mediated by aberrant PKN1 expression or activity or overexpression of PKN1, or enhances the therapeutic efficacy of another therapeutic agent.

In certain embodiments, the cancer or tumor harboring a PKN1 fusion is lung cancer (such as, e.g., lung squamous cell carcinoma.) In some embodiments the cancer or tumor harboring a PKN1 fusion is liver cancer (such as, e.g., hepatocellular carcinoma).

In some embodiments, the patient to be treated is suffering from lung cancer (e.g., lung squamous cell carcinoma), and the method for treating the condition comprises administering to the patient a therapeutically effective amount of a PKN1 inhibitor or a PKN1 fusion inhibitor as described above. In some embodiments, the patient to be treated is suffering from liver cancer (e.g., hepatocellular carcinoma), and the method for treating the condition comprises administering to the patient a therapeutically effective amount of a PKN1 inhibitor or a PKN1 fusion inhibitor as described above.

Screening Methods

Therapeutic agents, such as, e.g., PKN1 inhibitors, and PKN1 fusion inhibitors (gene fusion and fusion protein), used in the therapeutic methods of the invention can be evaluated using the screening assays described herein. Thus, the invention provides a method of identifying an agent useful for treating a condition mediated by aberrant PKN1 expression or activity, or overexpression of PKN1, such as, e.g., cancer or a tumor harboring a PKN1 fusion, such as, e.g., lung squamous cell carcinoma or hepatocellular carcinoma, comprising contacting a cell expressing a PKN1 gene fusion or PKN1 fusion protein with a candidate agent and using one of the detection methods referenced above to determine whether the expression level of the fusion is decreased or a biological function associated with the fusion is altered. In one embodiment, therapeutic agents can be evaluated in a cell-free system, e.g., a cell lysate or in a reconstituted system. In other embodiments, the therapeutic agents are evaluated in a cell in culture, e.g., a cell expressing a PKN1 fusion (e.g., a mammalian cell, a tumor cell or cell line, a recombinant cell). In yet other embodiments, the anti-cancer agents are evaluated in a cell in vivo (a PKN1 fusion-expressing cell present in a subject, e.g., an animal subject (e.g., an in vivo animal model).

Exemplary parameters to evaluate in determining the efficacy of a therapeutic agent for treating a condition mediated by aberrant PKN1 expression or activity, or overexpression of PKN1, such as, e.g., a cancer or a tumor harboring a PKN1 fusion include one or more of:

(i) a change in binding activity, e.g., direct binding of the candidate agent to a PKN1 fusion protein or a binding competition between a known ligand and the candidate agent to a PKN1 fusion protein;

(ii) a change in kinase activity, e.g., phosphorylation levels of a PKN1 fusion protein (e.g., an increased or decreased phosphorylation or autophosphorylation) or a change in phosphorylation of a target of a PKN1 kinase—in certain embodiments, a change in kinase activity, e.g., phosphorylation, is detected by any of western blot (e.g., using an anti-PKN1 antibody or a phosphor-specific antibody, detecting a shift in the molecular weight of a PKN1 fusion protein), mass spectrometry, immunoprecipitation, immunohistochemistry, immunomagnetic beads, among others;

(iii) a change in an activity of a cell containing a PKN1 fusion (e.g., a tumor cell or a recombinant cell), e.g., a change in proliferation, morphology, or tumorigenicity of the cell;

(iv) a change in tumor present in an animal subject, e.g., size, appearance, or proliferation of the tumor;

(v) a change in the level, e.g., expression level, of a PKN1 fusion protein or nucleic acid molecule; or (vi) a change in an activity of a signaling pathway involving PKN1, e.g., phosphorylation or activity of an interacting or downstream target, or expression level of a target gene.

In some embodiments, the PKN1 fusion is a TECR:PKN1 fusion or an ANXA4:PKN1 fusion.

In one embodiment, a change in the activity of a PKN1 fusion, or interaction of a PKN1 fusion with a downstream ligand detected in a cell free assay in the presence of a candidate agent indicates that the candidate agent will be effective as a therapeutic agent for treatment of a condition mediated by aberrant PKN1 expression or activity, or overexpression of PKN1, such as, e.g., a cancer or a tumor harboring a PKN1 fusion.

In other embodiments, a change in an activity of a cell expressing a PKN1 fusion, such as, e.g., TECR:PKN1 or ANXA4:PKN1, as described herein, (e.g., a mammalian cell, a tumor cell or cell line, a recombinant cell) is detected in a cell in culture. In one embodiment, the cell is a recombinant cell that is modified to express a PKN1 fusion nucleic acid, e.g., is a recombinant cell transfected with a PKN1 fusion nucleic acid. The transfected cell can show a change in response to the expressed PKN1 fusion, e.g., increased proliferation, changes in morphology, increased tumorigenicity, and/or acquired a transformed phenotype. A change in any of the activities of the cell, e.g., the recombinant cell, in the presence of the candidate agent can be detected. For example, a decrease in one or more of: proliferation, tumorigenicity, or transformed morphology, in the presence of the candidate agent can be indicative of an inhibitor of a PKN1 fusion. In other embodiments, a change in binding activity or phosphorylation of PKN1 or its interacting or downstream proteins or molecules as described herein is detected.

In yet other embodiment, a change in a tumor present in an animal subject (e.g., an in vivo animal model) is detected. In one embodiment, a tumor containing animal or a xenograft comprising cells expressing a PKN1 fusion (e.g., tumorigenic cells expressing a PKN1 fusion) is employed. The therapeutic agents can be administered to the animal subject and a change in the tumor is evaluated. In one embodiment, the change in the tumor includes one or more of a tumor growth, tumor size, tumor burden, or survival is evaluated. A decrease in one or more of tumor growth, tumor size, tumor burden, or an increased survival is indicative that the candidate agent is an inhibitor or modulator.

In another aspect of the invention provides a method or assay for screening for agents that modulate (e.g., inhibit) the expression or activity of a PKN1 fusion as described herein. The method includes contacting e.g., a PKN1 fusion, or a cell expressing a PKN1 fusion, with a candidate agent; and detecting a change in a parameter associated with a PKN1 fusion, e.g., a change in the expression or an activity of the PKN1 fusion. The method can, optionally, include comparing the treated parameter to a reference value, e.g., a control sample (e.g., comparing a parameter obtained from a sample with the candidate agent to a parameter obtained from a sample without the candidate agent). In one embodiment, if a decrease in expression or activity of the PKN1 fusion is detected, the candidate agent is identified as an inhibitor. In another embodiment, if an increase in expression or activity of the PKN1 fusion is detected, the candidate agent is identified as an activator. In certain embodiments, the PKN1 fusion is a PKN1 gene fusion or PKN1 fusion protein, such as, e.g., a TECR:PKN1 fusion or an ANXA4:PKN1 fusion.

In one embodiment, the contacting step is detected in a cell-free system, e.g., a cell lysate or in a reconstituted system. In other embodiments, the contacting step is detected in a cell in culture, e.g., a cell expressing a PKN1 fusion (e.g., a mammalian cell, a tumor cell or cell line, a recombinant cell). In yet other embodiments, the contacting step is detected in a cell in vivo (a PKN1 expressing cell present in a subject, e.g., an animal subject (e.g., an in vivo animal model).

Exemplary parameters evaluated in identifying an agent that modulates the activity of a PKN1 fusion (e.g., a TECR:PKN1 fusion or an ANXA4:PKN1 fusion) include one or more of:
  (i) a change in binding activity, e.g., direct binding of the candidate agent to a PKN1 fusion protein; a binding competition between a known ligand and the candidate agent to a PKN1 fusion protein,
  (ii) a change in kinase activity, e.g., phosphorylation levels of a PKN1 fusion protein (e.g., an increased or decreased phosphorylation or autophosphorylation) or a change in phosphorylation of a target of a PKN1 kinase—in certain embodiments, a change in kinase activity, e.g., phosphorylation, is detected by any of Western blot (e.g., using an anti-PKN1 antibody, or a phosphor-specific antibody, detecting a shift in the molecular weight of a PKN1 fusion protein), mass spectrometry, immunoprecipitation, immunohistochemistry, immunomagnetic beads, among others;
  (iii) a change in an activity of a cell containing a PKN1 fusion (e.g., a tumor cell or a recombinant cell), e.g., a change in proliferation, morphology or tumorigenicity of the cell;
  (iv) a change in tumor present in an animal subject, e.g., size, appearance, proliferation, of the tumor;
  (v) a change in the level, e.g., expression level, of a PKN1 fusion protein or nucleic acid molecule; or
  (vi) a change in an activity of a signaling pathway involving PKN1, e.g., phosphorylation or activity of an interacting or downstream target, or expression level of a target gene.

Methods for Validating PKN1 Fusions

PKN1 gene fusions (e.g., TECR:PKN1 gene fusions or ANXA4:PKN1 gene fusions) may be evaluated to ensure that the breakpoints are in-frame and can produce a protein product containing the full kinase domain, i.e., that the breakpoint occurs such that complete triplet codons are intact, and that the RNA sequence will produce a viable protein. The PKN1 gene fusion can be transfected into cells to confirm that the protein is functionally active with respect to kinase activity and oncogenic activity, cDNA encoding the PKN1 fusion protein can be produced by standard solid-phase DNA synthesis. Alternatively the PKN1 fusion cDNA can be produced by RT-PCR using tumor mRNA extracted from samples containing the gene fusion. The DNA amplified can be subcloned into an appropriate vector and characterized by DNA sequence analysis or in vitro/in vivo expression analyses.

Expression vectors containing the PKN1 gene fusion (such as, e.g., a PKN1 gene fusion, e.g., a TECR:PKN1 gene fusion or an ANXA4:PKN1 gene fusion) can be introduced into host cells to thereby produce a PKN1 fusion protein (such as, e.g., a PKN1 fusion protein, e.g., a TECR:PKN1 fusion protein or an ANXA4:PKN1 fusion protein). The PKN1 fusion protein expression vector can be a yeast expression vector, a vector for expression in insect cells, e.g., a baculovirus expression vector, or a vector suitable for expression in mammalian cells. Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell.

Cells harboring the expression vector carrying the recombinant PKN1 gene fusion can then be tested for production of the unique fusion protein via standard Western blotting using either an antibody probe that detects the gene product itself or that recognizes a tag peptide (e.g., FLAG tag) that can be added to the gene product via the expression vector (using standard, commercially available reagents). Western blotting can be used to confirm the ectopic expression of the encoded PKN1 fusion protein by comparing the samples from cells transfected with the vector containing the PKN1 gene fusion cDNA to cells transfected with the empty expression vector. The functional activity can be assessed by measuring the level of phosphorylation on the kinase or substrate. Comparison of the level of phosphorylation activity between the wild type (normal) form of PKN1 and the PKN1 fusion protein can indicate if the PKN1 fusion protein has elevated activity that could drive oncogenic activity. Whether the PKN1 gene fusion is oncogenic can be assessed by measuring capacity of the expressed PKN1 fusion protein to transform cells, that is, to enable cells to grow and proliferate under conditions which are not permissive for growth of normal cells. One commonly used method of measuring the transforming activity of a kinase is by assessing if expression of the gene product can allow BaF3 cells to grow in the absence of the growth factor IL3, which is required for the survival and growth of BaF3 cells. Another assay for measuring transforming activity is a soft agar growth assay. This is another standard method which tests the capacity of an introduced gene product to confer the ability to grow in a soft agar matrix, or anchorage-independent conditions. These methods and others can be used to test the oncogenic activity of a PKN1 gene fusion (such as, e.g., a TECR:PKN1 gene fusion or an ANXA4:PKN1 gene fusion) and provide a level of validation of a PKN1 fusion protein (such as, e.g., a TECR:PKN1 fusion protein or am ANXA4:PKN1 fusion protein) as a potential target for treating patients that harbor these fusions.

A change in an activity of a cell can be detected in a cell in culture. e.g., a cell expressing a fusion (e.g., a mammalian cell, a tumor cell or cell line, a recombinant cell). The transfected cell can show a change in response to the expressed fusion, e.g., increased proliferation, changes in morphology, increased tumorigenicity, and/or an acquired transformed phenotype.

To further validate the biological implication of the gene fusion, a change in any of the activities of the cell, e.g., the recombinant cell, in the presence of a known inhibitor of one of the fusion partners, e.g., a PKN1 inhibitor, can be detected. For example, a decrease in one or more of: proliferation, tumorigenicity, and transformed morphology, in the presence of the BETA inhibitor can be indicative of an inhibitor of a fusion. In other embodiments, a change in binding activity or phosphorylation of PKN1 or its interacting or downstream proteins or molecules is detected.

All publications and patents mentioned herein are hereby incorporated by reference in their entirety as if each individual publication or patent was specifically and individually indicated to be incorporated by reference. To the extent publications and patents or patent applications incorporated by reference contradict the disclosure contained in the specification, the specification will supersede any contradictory material. Unless otherwise required by context, singular terms shall include the plural and plural terms shall include the singular. The use of "or" means "and/or" unless stated otherwise. The use of the term "including," as well as other forms, such as "includes" and "included," is not limiting. All ranges given in the application encompass the endpoints unless stated otherwise.

Those skilled in the art will recognize, or be able to ascertain using no more than routine experimentation, many equivalents to the specific embodiments of the invention described herein. Such equivalents are intended to be encompassed by the following claims.

We claim:

1. A method for detecting in a patient a Protein Kinase N1 (PKN1) fusion that results in aberrant activity or expression of PKN1 or overexpression of PKN1, wherein the PKN1 fusion is a Trans-2,3-enoyl-CoA reductase (TECR):PKN1 or Annexin A4 (ANXA4):PKN1 fusion, said method comprising:
   a) contacting a biological sample obtained from the patient with an oligonucleotide that hybridizes to the fusion junction of a PKN1 gene fusion; and
   b) detecting binding between the PKN1 gene fusion and the oligonucleotide.

2. The method of claim 1, wherein the PKN1 gene fusion comprises:
   i) SEQ ID NO:1 or 3, or
   ii) a portion of SEQ ID NO:1 or 3, wherein the portion comprises a fusion junction between PKN1 and its fusion partner and the gene fusion encodes a polypeptide having PKN1 kinase activity.

3. The method of claim 1, wherein the oligonucleotide hybridizes under stringent conditions to:
   a) a fragment of SEQ ID NO:1 comprising nucleotides 6-25 of SEQ ID NO:1;
   b) a fragment of SEQ ID NO:3 comprising nucleotides 1-20 of SEQ ID NO:3; or
   c) a complementary oligonucleotide of a) or b).

4. The method of claim 1, wherein the patient is suffering from or susceptible to a cancer.

5. The method of claim 4, wherein the cancer is lung squamous cell carcinoma or hepatocellular carcinoma.

* * * * *

SEQUENCE LISTING

```
<160> NUMBER OF SEQ ID NOS: 4

<210> SEQ ID NO 1
<211> LENGTH: 1425
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 1
atgaagcatt acgaggtcac cttccgcaac cctgtcattg agaggattcc tcggctccga      60
cggcagaaga aaattttctc caagcagcaa gggaaggcgt tccagcgtgc taggcagatg     120
aacatcgatg tcgccacgtg ggtgcggctg ctccggaggc tcatccccaa tgccacgggc     180
acaggcacct ttagccctgg ggcttctcca ggatccgagg cccggaccac gggtgacata     240
tcggtggaga agctgaacct cggcactgac tcggacagct cacctcagaa gagctcgcgg     300
gatcctcctt ccagcccatc gagcctgagc tcccccatcc aggaatccac tgctcccgag     360
ctgccttcgg agacccagga gacccaggc cccgccctgt gcagccctct gaggaagtca     420
cctctgaccc tcgaagattt caagttcctg gcggtgctgg gcggggtca ttttgggaag     480 gtgctcctct ccgaattccg gcccagtggg gagctgttcg ccatcaaggc tctgaagaaa     540
ggggacattg tggcccgaga cgaggtggag agcctgatgt gtgagaagcg gatattggcg     600
gcagtgacca gtgcgggaca ccccttcctg gtgaacctct tcggctgttt ccagacaccg     660
gagcacgtgt gcttcgtgat ggagtactcg gccggtgggg acctgatgct gcacatccac     720
agcgacgtgt tctctgagcc ccgtgccatc ttttattccg cctgcgtggt gctgggccta     780
cagtttcttc acgaacacaa gatcgtctac agggacctga gttggacaa tttgctcctg     840 gacaccgagg gctacgtcaa gatcgcagac tttggcctct gcaaggaggg gatgggctat     900
ggggaccgga ccagcacatt ctgtgggacc ccggagttcc tggcccctga ggtgctgacg     960
gacacgtcgt acacgcgagc tgtggactgg tgggactgg gtgtgctgct ctacgagatg    1020
ctggttggcg agtccccatt cccagggat gatgaggagg aggtcttcga cagcatcgtc    1080
aacgacgagg ttcgctaccc ccgcttcctg tcggccgaag ccatcggcat catgagaagg    1140
ctgcttcgga ggaacccaga gcggaggctg ggatctagcg agagagatgc agaagatgtg    1200
aagaaacagc ccttcttcag gactctgggc tgggaagccc tgttggcccg gcgcctgcca    1260
```

```
ccgcccttig tgcccacgct gtccggccgc accgacgtca gcaacttcga cgaggagttc    1320
accggggagg cccccacact gagcccgccc cgcgacgcgc ggcccctcac agccgcggag    1380
caggcagcct tcctggactt cgacttcgtg gccgggggct gctag                    1425
```

<210> SEQ ID NO 2
<211> LENGTH: 474
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 2

```
Met Lys His Tyr Glu Val Thr Phe Arg Asn Pro Val Ile Glu Arg Ile
1               5                   10                  15

Pro Arg Leu Arg Arg Gln Lys Lys Ile Phe Ser Lys Gln Gln Gly Lys
            20                  25                  30

Ala Phe Gln Arg Ala Arg Gln Met Asn Ile Asp Val Ala Thr Trp Val
        35                  40                  45

Arg Leu Leu Arg Leu Ile Pro Asn Ala Thr Gly Thr Gly Thr Phe
    50                  55                  60

Ser Pro Gly Ala Ser Pro Gly Ser Glu Ala Arg Thr Thr Gly Asp Ile
65                  70                  75                  80

Ser Val Glu Lys Leu Asn Leu Gly Thr Asp Ser Asp Ser Ser Pro Gln
                85                  90                  95

Lys Ser Ser Arg Asp Pro Pro Ser Pro Ser Ser Leu Ser Ser Pro
            100                 105                 110

Ile Gln Glu Ser Thr Ala Pro Glu Leu Pro Ser Glu Thr Gln Glu Thr
        115                 120                 125

Pro Gly Pro Ala Leu Cys Ser Pro Leu Arg Lys Ser Pro Leu Thr Leu
    130                 135                 140

Glu Asp Phe Lys Phe Leu Ala Val Leu Gly Arg Gly His Phe Gly Lys
145                 150                 155                 160

Val Leu Leu Ser Glu Phe Arg Pro Ser Gly Glu Leu Phe Ala Ile Lys
                165                 170                 175

Ala Leu Lys Lys Gly Asp Ile Val Ala Arg Asp Glu Val Glu Ser Leu
            180                 185                 190

Met Cys Glu Lys Arg Ile Leu Ala Ala Val Thr Ser Ala Gly His Pro
        195                 200                 205

Phe Leu Val Asn Leu Phe Gly Cys Phe Gln Thr Pro Glu His Val Cys
    210                 215                 220

Phe Val Met Glu Tyr Ser Ala Gly Gly Asp Leu Met Leu His Ile His
225                 230                 235                 240

Ser Asp Val Phe Ser Glu Pro Arg Ala Ile Phe Tyr Ser Ala Cys Val
                245                 250                 255

Val Leu Gly Leu Gln Phe Leu His Glu His Lys Ile Val Tyr Arg Asp
            260                 265                 270

Leu Lys Leu Asp Asn Leu Leu Leu Asp Thr Glu Gly Tyr Val Lys Ile
        275                 280                 285

Ala Asp Phe Gly Leu Cys Lys Glu Gly Met Gly Tyr Gly Asp Arg Thr
    290                 295                 300

Ser Thr Phe Cys Gly Thr Pro Glu Phe Leu Ala Pro Glu Val Leu Thr
305                 310                 315                 320
```

```
Asp Thr Ser Tyr Thr Arg Ala Val Asp Trp Trp Gly Leu Gly Val Leu
                325                 330                 335

Leu Tyr Glu Met Leu Val Gly Ser Pro Phe Pro Gly Asp Asp Glu
            340                 345                 350

Glu Glu Val Phe Asp Ser Ile Val Asn Asp Glu Val Arg Tyr Pro Arg
            355                 360                 365

Phe Leu Ser Ala Glu Ala Ile Gly Ile Met Arg Arg Leu Leu Arg Arg
    370                 375                 380

Asn Pro Glu Arg Arg Leu Gly Ser Ser Glu Arg Asp Ala Glu Asp Val
385                 390                 395                 400

Lys Lys Gln Pro Phe Phe Arg Thr Leu Gly Trp Glu Ala Leu Leu Ala
                405                 410                 415

Arg Arg Leu Pro Pro Pro Phe Val Pro Thr Leu Ser Gly Arg Thr Asp
                420                 425                 430

Val Ser Asn Phe Asp Glu Glu Phe Thr Gly Glu Ala Pro Thr Leu Ser
            435                 440                 445

Pro Pro Arg Asp Ala Arg Pro Leu Thr Ala Ala Glu Gln Ala Ala Phe
        450                 455                 460

Leu Asp Phe Asp Phe Val Ala Gly Gly Cys
465                 470

<210> SEQ ID NO 3
<211> LENGTH: 1107
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 3
atggccatga gctcccccat ccaggaatcc actgctcccg agctgccttc ggagacccag      60
gagaccccag ccccgccct gtgcagccct ctgaggaagt cacctctgac cctcgaagat     120
ttcaagttcc tggcggtgct gggccggggt cattttggga aggtgctcct ctccgaattc     180
cggcccagtg gggagctgtt cgccatcaag gctctgaaga aggggacat tgtggcccga     240 gacgaggtgg agagcctgat gtgtgagaag cggatattgg cggcagtgac cagtgcggga     300
caccccttcc tggtgaacct cttcggctgt ttccagacac cggagcacgt gtgcttcgtg     360
atggagtact cggccggtgg ggacctgatg ctgcacatcc acagcgacgt gttctctgag     420
ccccgtgcca tcttttattc cgcctgcgtg gtgctgggcc tacagtttct tcacgaacac     480
aagatcgtct acagggacct gaagttggac aatttgctcc tggacaccga gggctacgtc     540
aagatcgcag actttggcct ctgcaaggag gggatgggct atgggaccg gaccagcaca     600 ttctgtggga ccccggagtt cctggcccct gaggtgctga cggacacgtc gtacacgcga     660
gctgtggact ggtggggact gggtgtgctg ctctacgaga tgctggttgg cgagtcccca     720
ttcccagggg atgatgagga ggaggtcttc gacagcatcg tcaacgacga ggttcgctac     780
ccccgcttcc tgtcggccga agccatcggc atcatgagaa ggctgcttcg gaggaaccca     840
gagcggaggc tgggatctag cgagagagat gcagaagatg tgaagaaaca gcccttcttc     900
aggactctgg gctgggaagc cctgttggcc cggcgcctgc caccgccctt tgtgcccacg     960
ctgtccggcc gcaccgacgt cagcaacttc gacgaggagt tcaccgggga ggcccccaca    1020
ctgagcccgc cccgcgacgc gcggcccctc acagccgcgg agcaggcagc cttcctggac    1080
ttcgacttcg tggccggggg ctgctag                                         1107
```

<210> SEQ ID NO 4
<211> LENGTH: 368
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 4

```
Met Ala Met Ser Ser Pro Ile Gln Glu Ser Thr Ala Pro Glu Leu Pro
1               5                   10                  15
Ser Glu Thr Gln Glu Thr Pro Gly Pro Ala Leu Cys Ser Pro Leu Arg
            20                  25                  30
Lys Ser Pro Leu Thr Leu Glu Asp Phe Lys Phe Leu Ala Val Leu Gly
        35                  40                  45
Arg Gly His Phe Gly Lys Val Leu Leu Ser Glu Phe Arg Pro Ser Gly
    50                  55                  60
Glu Leu Phe Ala Ile Lys Ala Leu Lys Lys Gly Asp Ile Val Ala Arg
65                  70                  75                  80
Asp Glu Val Glu Ser Leu Met Cys Glu Lys Arg Ile Leu Ala Ala Val
                85                  90                  95
Thr Ser Ala Gly His Pro Phe Leu Val Asn Leu Phe Gly Cys Phe Gln
            100                 105                 110
Thr Pro Glu His Val Cys Phe Val Met Glu Tyr Ser Ala Gly Gly Asp
        115                 120                 125
Leu Met Leu His Ile His Ser Asp Val Phe Ser Glu Pro Arg Ala Ile
    130                 135                 140
Phe Tyr Ser Ala Cys Val Val Leu Gly Leu Gln Phe Leu His Glu His
145                 150                 155                 160
Lys Ile Val Tyr Arg Asp Leu Lys Leu Asp Asn Leu Leu Leu Asp Thr
                165                 170                 175
Glu Gly Tyr Val Lys Ile Ala Asp Phe Gly Leu Cys Lys Glu Gly Met
            180                 185                 190
Gly Tyr Gly Asp Arg Thr Ser Thr Phe Cys Gly Thr Pro Glu Phe Leu
        195                 200                 205
Ala Pro Glu Val Leu Thr Asp Thr Ser Tyr Thr Arg Ala Val Asp Trp
    210                 215                 220
Trp Gly Leu Gly Val Leu Leu Tyr Glu Met Leu Val Gly Glu Ser Pro
225                 230                 235                 240
Phe Pro Gly Asp Asp Glu Glu Val Phe Asp Ser Ile Val Asn Asp
                245                 250                 255
Glu Val Arg Tyr Pro Arg Phe Leu Ser Ala Glu Ala Ile Gly Ile Met
            260                 265                 270
Arg Arg Leu Leu Arg Arg Asn Pro Glu Arg Arg Leu Gly Ser Ser Glu
        275                 280                 285
Arg Asp Ala Glu Asp Val Lys Lys Gln Pro Phe Phe Arg Thr Leu Gly
    290                 295                 300
Trp Glu Ala Leu Leu Ala Arg Arg Leu Pro Pro Pro Phe Val Pro Thr
305                 310                 315                 320
Leu Ser Gly Arg Thr Asp Val Ser Asn Phe Asp Glu Glu Phe Thr Gly
                325                 330                 335
Glu Ala Pro Thr Leu Ser Pro Arg Asp Ala Arg Pro Leu Thr Ala
            340                 345                 350
```

-continued

```
Ala Glu Gln Ala Ala Phe Leu Asp Phe Asp Phe Val Ala Gly Gly Cys
            355                 360                 365
```